(12) United States Patent
Matsuoka

(10) Patent No.: US 9,696,150 B2
(45) Date of Patent: Jul. 4, 2017

(54) OVERLAY ERROR MEASURING DEVICE AND COMPUTER PROGRAM

(71) Applicant: HITACHI HIGH-TECHNOLOGIES CORPORATION, Tokyo (JP)

(72) Inventor: Ryoichi Matsuoka, Tokyo (JP)

(73) Assignee: HITACHI HIGH-TECHNOLOGIES CORPORATION, Tokyo (JP)

(*) Notice: Subject to any disclaimer, the term of this patent is extended or adjusted under 35 U.S.C. 154(b) by 11 days.

(21) Appl. No.: 14/407,896

(22) PCT Filed: Jun. 10, 2013

(86) PCT No.: PCT/JP2013/065909
§ 371 (c)(1),
(2) Date: Dec. 12, 2014

(87) PCT Pub. No.: WO2013/187343
PCT Pub. Date: Dec. 19, 2013

(65) Prior Publication Data
US 2015/0136976 A1    May 21, 2015

(30) Foreign Application Priority Data
Jun. 15, 2012   (JP) ................................ 2012-135299

(51) Int. Cl.
*G01B 15/00*    (2006.01)
*G01N 23/225*   (2006.01)
(Continued)

(52) U.S. Cl.
CPC ......... *G01B 15/00* (2013.01); *G01N 23/2251* (2013.01); *G03F 7/70633* (2013.01);
(Continued)

(58) Field of Classification Search
CPC combination set(s) only.
See application file for complete search history.

(56) References Cited

U.S. PATENT DOCUMENTS

| 8,019,161 B2 | 9/2011 | Morokuma et al. |
| 2003/0021465 A1* | 1/2003 | Adel .................. G03F 7/70633 382/151 |

(Continued)

FOREIGN PATENT DOCUMENTS

| JP | 2003279341 A | 10/2003 |
| JP | 2005-322748 A | 11/2005 |

(Continued)

OTHER PUBLICATIONS

English language translation International Search Report PCT/JP2013/065909 dated Aug. 6, 2013.
(Continued)

*Primary Examiner* — Phillip A Johnston
*Assistant Examiner* — Hsien Tsai
(74) *Attorney, Agent, or Firm* — McDermott Will & Emery LLP

(57) ABSTRACT

The purpose of the present invention is to provide an overlay error measuring device for correcting a pattern displacement other than an overlay error to thereby achieve high-precision overlay error measurement. To accomplish the abovementioned purpose, the present invention proposes an overlay error measuring device which measures a dimension between a plurality of patterns belonging to different layers using a signal obtained by a charged particle beam device, and when measuring the dimension, corrects an amount corresponding to a pattern shift due to an optical proximity effect and measures the dimension between the plurality of patterns.

8 Claims, 18 Drawing Sheets

OVERLAY MEASUREMENT PORTION (SYMMETRICAL SHAPE)

(51) Int. Cl.
*H01J 37/22* (2006.01)
*G03F 7/20* (2006.01)
*H01J 37/28* (2006.01)

(52) U.S. Cl.
CPC ............ *H01J 37/222* (2013.01); *H01J 37/28* (2013.01); *G01N 2223/418* (2013.01); *G01N 2223/6113* (2013.01); *H01J 2237/24578* (2013.01); *H01J 2237/24592* (2013.01); *H01J 2237/2817* (2013.01)

(56) References Cited

U.S. PATENT DOCUMENTS

| | | | |
|---|---|---|---|
| 2003/0093767 A1* | 5/2003 | Murai | B82Y 10/00 430/30 |
| 2006/0108524 A1 | 5/2006 | Nagatomo et al. | |
| 2007/0023653 A1 | 2/2007 | Toyoda et al. | |
| 2007/0210252 A1 | 9/2007 | Miyamoto et al. | |
| 2007/0221842 A1* | 9/2007 | Morokuma | G01N 23/2251 250/307 |
| 2008/0130982 A1 | 6/2008 | Kitamura et al. | |
| 2012/0098953 A1* | 4/2012 | Kotaki | H01J 37/222 348/80 |
| 2012/0300054 A1 | 11/2012 | Mito et al. | |

FOREIGN PATENT DOCUMENTS

| | | |
|---|---|---|
| JP | 2006-126532 A | 5/2006 |
| JP | 2006351888 A | 12/2006 |
| JP | 2007248087 A | 9/2007 |
| JP | 2007250528 A | 9/2007 |
| JP | 2008164593 A | 7/2008 |
| JP | 2011-23273 A | 2/2011 |
| WO | 2011090111 A1 | 7/2011 |
| WO | 2013089096 A1 | 6/2013 |

OTHER PUBLICATIONS

Office Action Korean Patent Application No. 10-2014-7031623 dated Mar. 17, 2016.

* cited by examiner

FIG.11

| Pattern type | Adjacent pattern | | | | Shift amount | Direction |
|---|---|---|---|---|---|---|
| A | b | | | | $x_1, y_1$ | $\theta_1$ |
| B | | | | | | |
| C | | | | | | |
| D | | | | | | |
| E | | | | | | |

FIG.12
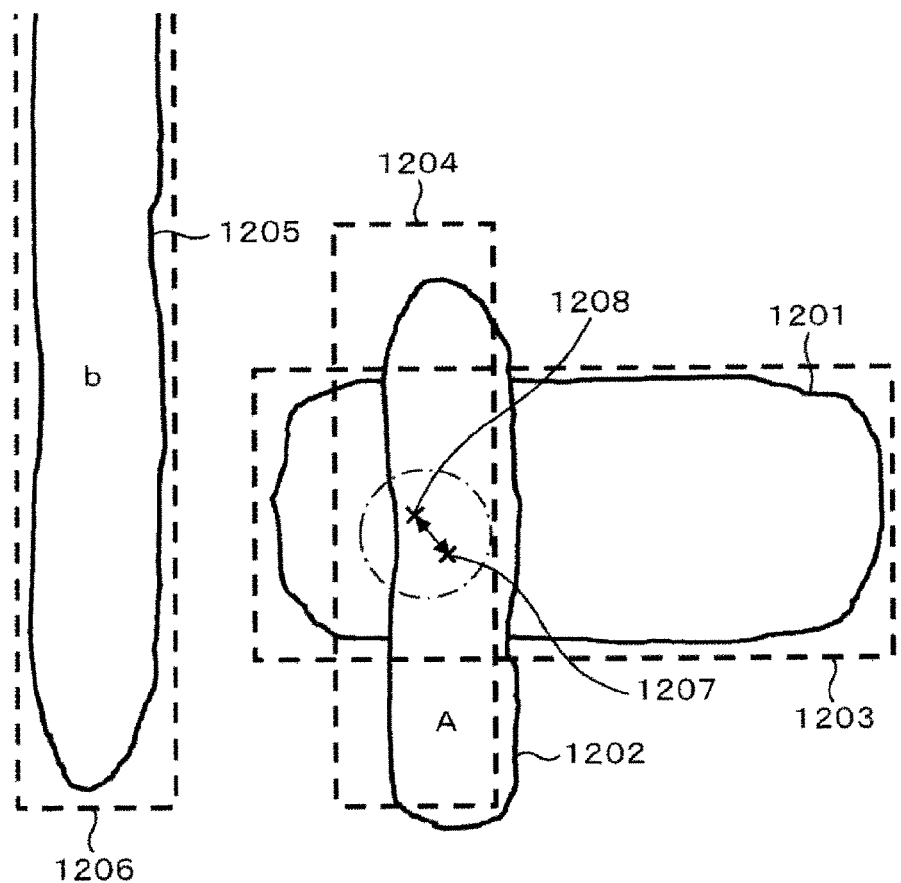
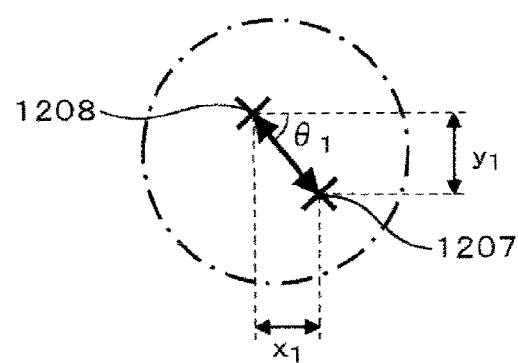

OVERLAY ERROR MEASURING DEVICE AND COMPUTER PROGRAM

CROSS REFERENCE TO RELATED APPLICATIONS

This application is the U.S. National Phase of PCT/JP2013/065909 filed Jun. 10, 2013which claims priority from Japanese Patent Application No. 2012-135299 filed Jun. 15, 2012. The subject matter of each is incorporated herein by reference in entirety.

TECHNICAL FIELD

The present invention relates to a semiconductor measurement device, a computer program for allowing a computer to execute measurement or a recording medium thereof, and more particularly to a measuring device or the like adaptable for measurement of overlay errors of a sample with a plurality of layers laminated.

BACKGROUND ART

In recent years, owing to advances in microfabrication technologies in the manufacture of semiconductor devices, the miniaturization of fabrication patterns is remarkable, raising a need for large-magnification measurement in inspection and measurement processes in the semiconductor production. Especially, in semiconductor fabrication processes, various kinds of resolution enhancement technology (RET) are employed to perform per-layer process treatment, such as advanced exposure and etching or the like; then, superposition with the next layer is performed to form circuit patterns sequentially.

Management of the superposition in this case is done by means of an optical testing/inspection device using dedicated alignment marks.

More specifically, although dedicated patterns for superposition are disposed in the periphery (e.g., at four corners) of a shot area, which is a unit of exposure, for management of a superposition situation of this shape by using an optical inspection device, high-accuracy superposition management is important in order to realize high yields, resulting in optics-based management approaching its limit.

Additionally, in optical scheme-based systems, there are cases where the superposition measurement experiences an error increase due to the influence of transfer-pattern distortions caused by the lens aberration of an exposure device. To cope with this, it becomes necessary to exclude the lens aberration-based error factors by execution of superposition measurement of fine patterns in local regions.

Patent Literature 1 discloses a technique for measuring dimensions between patterns belonging to a plurality of layers. According to the measurement method disclosed in Patent Literature 1, it is possible to perform it by using an image representing the actually formed "real" patterns. Thus, it is possible to measure inter-pattern dimensions with very high accuracy.

CITATION LIST

Patent Literatures

Patent Literature 1: JP-A-2007-248087 (corresponding U.S. Pat. No. 8,019,161)

SUMMARY OF INVENTION

Technical Problem

According to the technique for performing measurement between edges of real patterns in the way disclosed in Patent Literature 1, it is possible to perform the interpattern dimension measurement with nano-level accuracy; however, it was revealed by investigation of the inventors of this invention that these are dimension error factors given below.

By the quest for higher integration of semiconductor devices in recent years, the distance between patterns is becoming extremely shorter. This results in occurrence of the following phenomenon: when compared to design data (layout data), a pattern shifts undesirably due to an optical proximity effect (OPE). In the presence of interlayer superposition errors, the inter-edge dimensions between layers must contain such pattern shift due to superposition errors and OPE. By mere execution of interpattern dimension measurement, it is difficult to grasp exact overlay errors.

Effective suppression of such errors of overlay error measurement, which errors become obvious as high-accuracy measurement is enabled in this way and become greater with advances in miniaturization of semiconductor devices, makes it possible to achieve high-accuracy overlay error measurement. An overlay error measurement device which aims to correct pattern deviation other than overlay errors to thereby perform high-accuracy overlay error measurement and a computer program therefor are proposed below.

Solution to Problem

As one form for attaining the foregoing object, there are proposed below an overlay error measuring device having an arithmetic processing device which performs measurement of patterns formed on a sample based on an image obtained by a charged particle beam device, wherein the arithmetic processing device uses a signal obtained by the charged particle beam device to measure dimensions between a plurality of patterns that belong to different layers and executes dimension measurement between the plurality of patterns by correcting a pattern shift component occurred due to the optical proximity effect, and a computer program for realization of the measurement.

Also proposed are an overlay error measuring device which selects for correction a symmetry pattern with an array of patterns of the same shape on layout data as the pattern to be applied the above-stated pattern shift component caused by the optical proximity effect, and a computer program for realization of the measurement.

Advantageous Effects of Invention

According to the arrangement stated above, it becomes possible to achieve accurate overlay error measurement while at the same time suppressing the influence of the pattern shift caused by optical proximity effect.

BRIEF DESCRIPTION OF DRAWINGS

FIG. 11 A diagram shows one example of a database used for correction of OPE-caused pattern shift.

FIG. 12 A diagram shows an overview of OPE-caused pattern shift.

DESCRIPTION OF EMBODIMENTS

Figure 1:
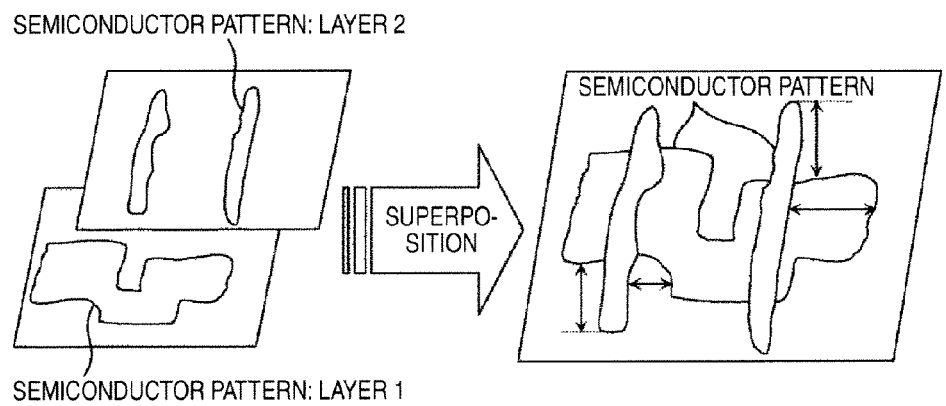
FIG. 1 A diagram shows that a semiconductor circuit is constituted by superposition of two layers.

A summary of overlay measurement will be described by using some of the accompanying drawings below. FIG. 1 is a diagram showing one example of a pattern which is an object under overlay measurement. A semiconductor wafer is made up of a plurality of laminated layers; by this multilayer lamination, a semiconductor circuit is constituted. FIG. 1 is a diagram showing a transistor structure having a diffusion layer in lower layer (layer 1) and a gate layer in upper layer (layer 2). In embodiments explained below, examples will be explained which perform overlay measurement by chiefly measuring relative positions of these two layers.

Overlay control/management in semiconductor fabrication processes and its relating measurement technique are important and play a key role in semiconductor mass-production processes. And, recent advances in microfabrication technology lead to a demand for further increased accuracy. In particular, when the required superposition accuracy becomes less than about 5 nm, error factors occurrable in actually fabricated device patterns (such as thermal aberration of lens, STI stress, etc.) are no longer ignorable.

In a technique for disposing dedicated patterns for superposition in the periphery (e.g., at four corners) of a shot area defined by an exposure device and for managing a superposition situation of this shape by using an optical testing/inspection device, there is a limit of its resolving power of the waveform of light of the optical inspection device; so, it is difficult to evaluate superposition errors while retaining sufficient accuracy. Additionally, the deviation of patterns in wide areas within a shot is becoming larger due to the influence of the thermal aberration of lens of the exposure device. In superposition management of patterns at the corners of the shot, it reaches a limit in terms of the accuracy. Furthermore, in STI layers of transistors, there is a variation in gate shape due to the influence of gate shape stresses caused by the influence of peripheral contact-holes.

It is thus desired to perform superposition management using real patterns (i.e., data with imaging processing applied to real pattern shapes).

Accordingly, in this embodiment, there will be explained an apparatus for performing overlay measurement based on a signal(s) obtainable by a charged particle beam device, such as an ion beam microscope or a scanning electron microscope capable of acquiring images at high magnification ratios which cannot be obtained by optical inspection devices, a computer program for causing a computer to execute this measurement, and a recording medium storing therein the computer program.

The scanning electron microscope (SEM) is capable of performing dimension measurement with accuracy of less than or equal to 5 nm. In this embodiment, an explanation will be given of an example which uses for the overlay measurement a critical dimension scanning electron microscope (CD-SEM) which measures the dimension of a pattern or dimensions between a plurality of patterns.

The CD-SEM is able to acquire the image of a field of view having its size of less than or equal to 100 nm for example; however, upon execution of overlay measurement, because of its ability to perform observation and measurement at very high magnification ratios, there are measurement error factors given below.

In exposure processes for respective layers of semiconductor devices, pattern formation is performed using what is called the resolution enhancement technology (RET) that actively leverages the optical proximity effect. The RET includes optical proximity correction (OPC) processing used in a diffusion layer formation process, gate layer formation process and wiring process, and sub-resolution assist feature (SRAF) pattern processing typified by a contact-hole forming process.

In the case of performing pattern evaluation based on SEM images representative of patterns with these processing treatments applied thereto, it can sometimes happen that resolution is done while letting the position of a pattern be shifted or deviated from its original position due to the influence of an optical proximity effect (OPE) with the pattern shape and pattern topology serving as factors.

In other words, in cases where there is an overlay error, this results in coexistence of pattern deviation and OPE-caused pattern shift in a mixed manner, causing appropriate evaluation of overlay error to become difficult in some cases. In this embodiment, an explanation will be given of an apparatus for suppressing overlay error measurement errors particularly based on OPE-caused pattern position deviation to thereby perform accurate overlay error measurement. More specifically, an example will be explained which performs control/management of superposition of upper and lower layers after having corrected a position deviation component based on the OPE or else and executed position deviation canceling.

Figure 9:
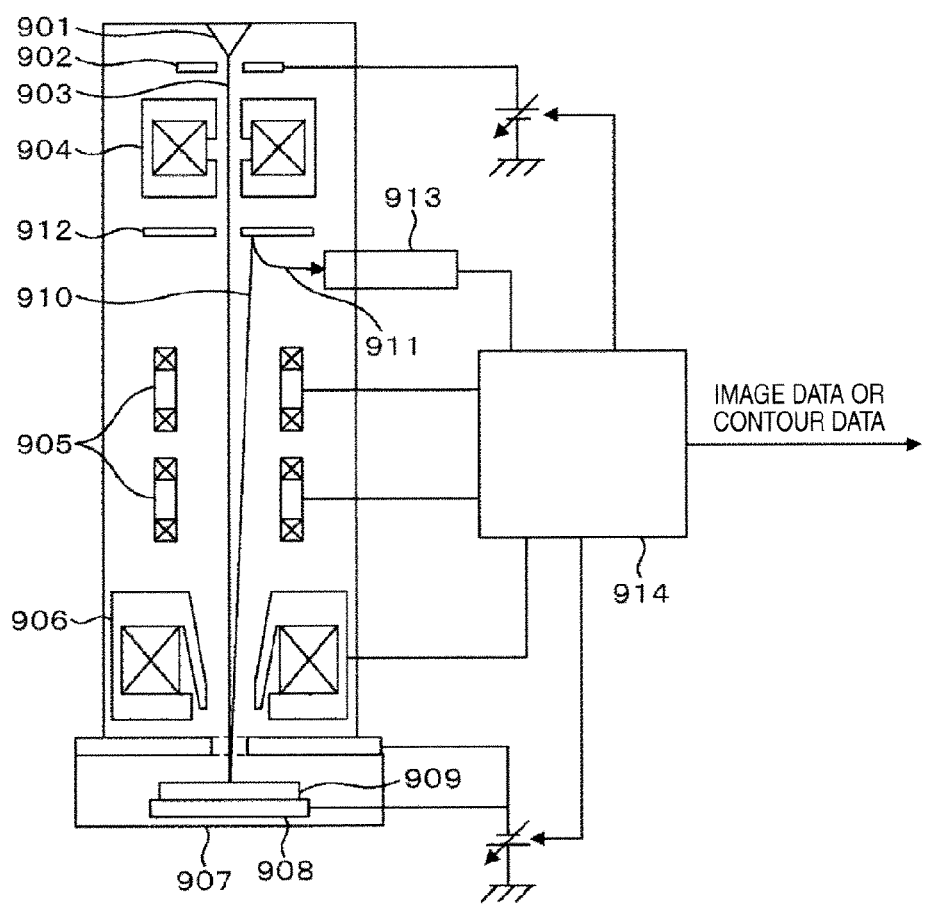
FIG. 9 A diagram shows one example of a scanning electron microscope.

FIG. 9 is a diagram showing one example of the scanning electron microscope used to acquire an image for the pattern measurement use. An electron beam 903 which was drawn out of an electron source 901 by a pullout electrode 902 and accelerated by an acceleration electrode that is not shown in Figure is narrowed by a condenser lens 904 which is one form of a focusing lens and, thereafter, driven by a scanning deflector 905 to scan the top surface of a workpiece or sample 909 in a one- or two-dimensional manner. The electron beam 903 is decelerated by a negative voltage being applied to an electrode that is built in a sample table 908 and is converged by the lens action of an objective lens 906 to be irradiated onto the sample 909.

Upon irradiation of the electron beam 903 onto the sample 909 that is disposed within a vacuum chamber 907, electrons 910 such as secondary electrons and backscatter electrons are released from this irradiated part. The released electrons 910 are accelerated in an electron source direction by acceleration action based on a negative voltage being applied to the sample and then collide with a conversion electrode 912, generating secondary electrons 911. The secondary electrons 911 released from conversion electrode 912 are captured by a detector 913, causing an output of the detector 913 to vary depending on the quantity of captured secondary electrons. In response to this output, a display device that is not shown in Figure changes in brightness. For example, in the case of forming a two-dimensional image, an image of scan region is created by establishing synchronization between a deflection signal supplied to the scanning deflector 905 and an output of detector 913. The scanning electron microscope shown exemplarily in FIG. 9 also includes a deflector (not shown in Figure) for moving the electron beam's scanning region. This deflector is used to form images of patterns having the same shape existing at different positions. This deflector is also called the image shift deflector, which enables position movement of a field of view (FOV) of the electron microscope. Another configuration may also be employed which combines the image shift deflector and the scanning deflector into a common deflector and which superimposes an image shifting signal and a scanning signal and supplies it to the deflector.

It should be noted that although in the example of FIG. 9 an example is explained which detects the electrons released from a sample after having once converted at the conversion electrode, the invention should not exclusively be limited to this arrangement and may alternatively be modified to employ another arrangement—for example, a scheme for disposing the detection planes of an electron double-image tube and detector on the orbit of accelerated electrons. A control device 914 has functions of controlling respective components of the scanning electron microscope and forming images based on detected electrons and also has a function of measuring the width of an on-sample formed pattern based on an intensity distribution of detected electrons, called the line profile.

Figure 10:
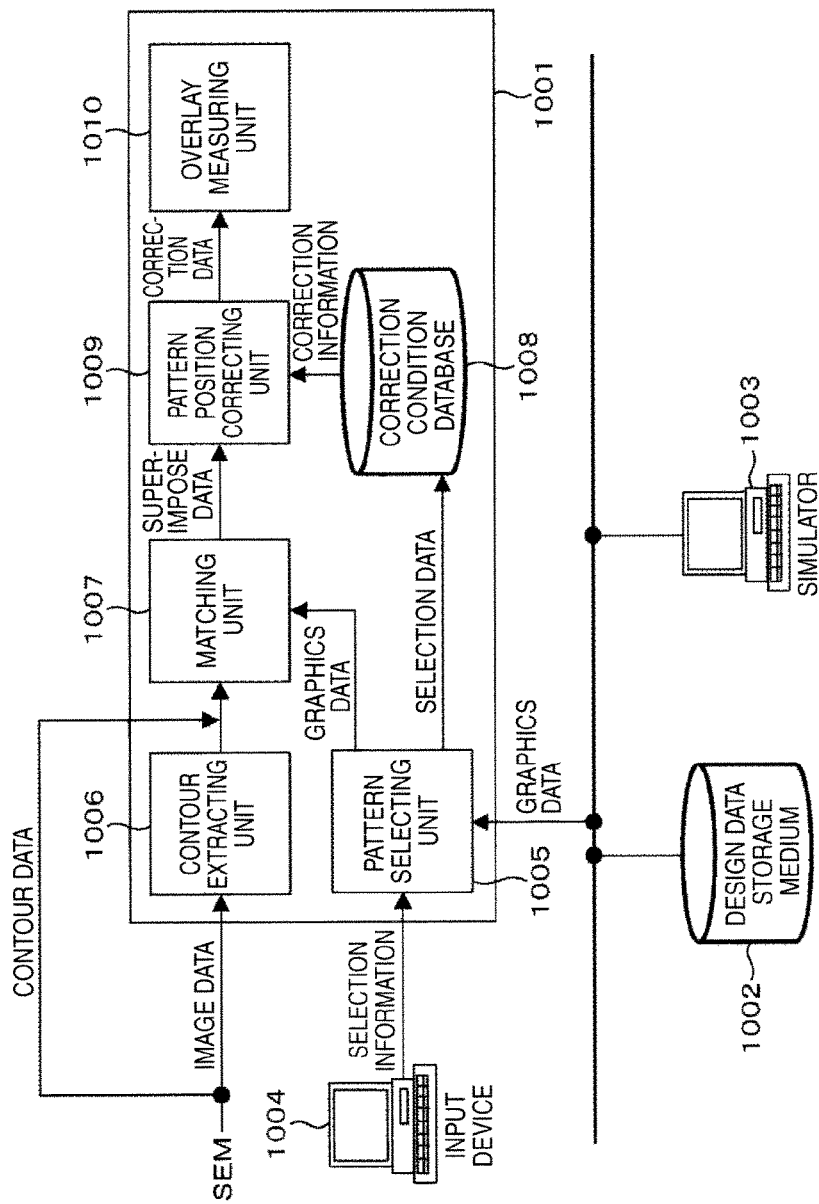
FIG. 10 A diagram shows one example of a semiconductor measurement system.

FIG. 10 is a diagram showing one exemplary semiconductor measurement system. This system includes an overlay error measuring device 1001 which executes overlay error measurement based on a signal(s) obtained by SEM (e.g., image data and/or contour data), a design data storage medium 1002 storing therein design data, a simulator 1003 which executes simulation based on the design data, and an input device 1004 which inputs information required for the measurement. The design data is represented, for example, by GDS format or OASIS format or the like, and is saved in a predetermined form. Note here that the design data may have any available format type as far as it is displayable and treatable as graphics data by design data-displaying software.

A pattern selecting unit 1005 selects a pattern to be subjected to the overlay error measurement based on the information inputted from the input device 1004. This selection data is stored as a measurement condition for example, and saved in a predetermined storage medium as an operation program (recipe) of the SEM and that of overlay error measuring device 1001. A contour extracting unit 1006 extracts a contour based on the image data acquired by the SEM. The contour extraction is executed, for example, by performing edge-thinning after having binarized the SEM image. Optionally, in the case of forming a contour of higher accuracy, a process may be employed which includes the steps of preparing a brightness profile in a direction at right angles to the thinning-applied edge and defining as the edge a portion having a prescribed level of brightness. In cases where the SEM has its built-in contour conversion functionality, the contour extracting unit 1006 is made redundant.

A matching unit 1007 executes pattern matching between the contour data and either one of design data-based graphics data and design data-based simulation data. A detailed explanation of the matching will be given later. A pattern position correcting unit 1009 applies position correction selectively to a pattern in superimposition data of the layout data or else and the contour data, which pattern is selected by the pattern selecting unit 1005. A correction condition is stored in a correction condition database 1008, for executing selective pattern movement based on the correction condition. An overlay measuring unit executes overlay error measurement based on the corrected data that was revised by the pattern position correcting unit 1009.

As stated above, in the case of superposition measurement using real patterns, it can sometimes happen that patterns which have been transferred to one layer are position-shifted or distorted due to the influence of the optical proximity effect. If this is the case, a need is felt to perform overlay evaluation by exclusion of this shift/distortion component. More specifically, it is required to perform separation or "carving" to distinguish this pattern shift from interlayer pattern position deviation for detecting a true overlay error(s).

[Embodiment 1]

In this embodiment, overlay error measurement is executed principally in a procedure which follows.

Step 1: Selection of overlay measuring object pattern
Step 2: Automatic generation of measurement recipe
Step 3: Image acquisition by execution of the recipe
Step 4: Execution of OPE correction
Step 5: Overlay error measurement A detailed explanation of each step will be given using some of the accompanying drawings below.

(1) Selection of Overlay Measuring Object Pattern

First of all, at this step, semiconductor design data (layout data) or simulation data is used to perform selection of an overlay measuring object pattern. In this case, for example, a specific pattern (e.g., a transistor or else consisting of a two-layer structure, such as a diffusion layer and a gate layer) and its coordinates and also the size of an image acquisition region (field of view) are selected on the layout data or the simulation data, thereby determining a pattern or an evaluation region. The input device 1004 is for selecting a desired measuring object from graphics data, such as the layout data or simulation data being stored in a design data storage medium 1002.

(2) Automatic Generation of Measurement Recipe

What is next performed is to acquire images of the selected pattern and evaluation region and automatically generate a recipe for execution of measurement based on such images acquired. As the design data contains pattern coordinate information or the like, the SEM's stage movement condition and a pattern necessary for addressing are selected automatically in such a way that the field of view of SEM or else is position-assigned to this coordinate, while executing setup of a length-measurement box in an automated or semi-automated manner. The addressing pattern is selected so as to ensure that the measuring object pattern and the addressing pattern are positioned, for example, in the SEM's beam-shiftable area. The addressing pattern is such that a shape-unique one is selected in order to avoid false detection.

Figure 13:
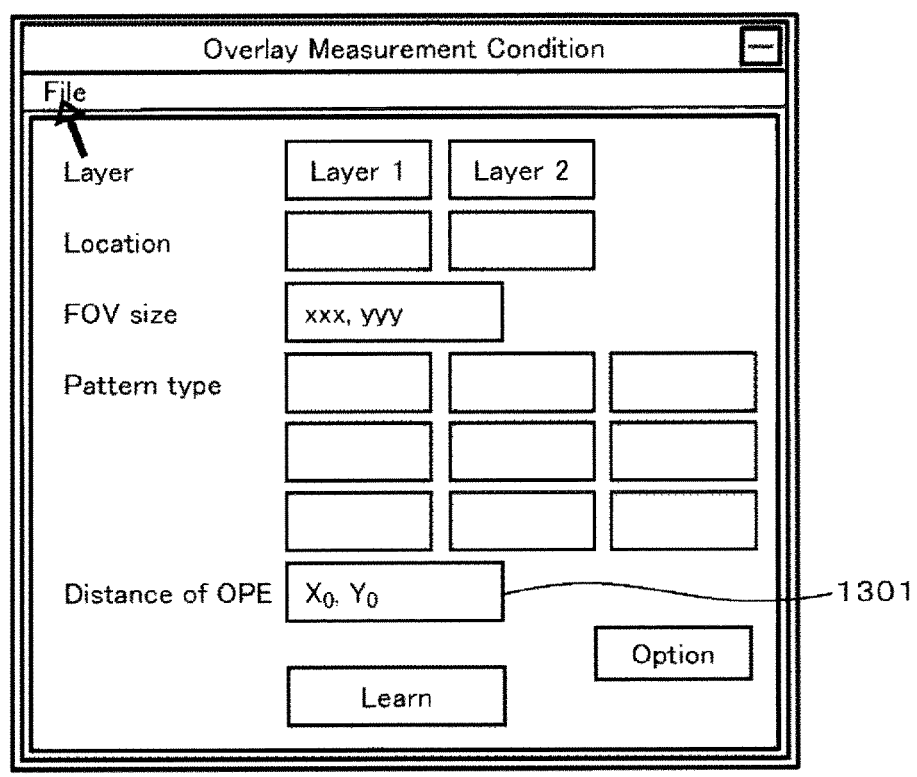
FIG. 13 A diagram shows one example of GUI screen for setup of an overlay error measurement condition.

FIG. 13 is a diagram showing one example of a graphical user interface (GUI) screen or "window" used for setting a measurement condition(s). This window is displayed, for example, on the display screen of input device 1004. With this GUI window, it becomes possible to select a layer which becomes the overlay evaluation object (Layer), an evaluation object region or a pattern coordinate (position: Location), and SEM's scan area size (FOV size). Based on the input to this window, stage movement and beam deflection conditions and others are set up automatically. Also provided are a window (Pattern Type) for selecting the kind of a pattern that becomes the measuring object and a window (Distance of OPE) 1301 for selecting the distance of optical proximity effect (OPE).

To the window 1301, information relating to the distance between the measuring object and its adjacent pattern is inputted. The optical proximity effect-caused pattern shift depends chiefly on the distance between the measuring object and its neighboring pattern: the shorter the distance, the greater the influence. Therefore, when performing overlay measurement after having applied position correction to those less than the distance inputted to the window for example in accordance with the prestored database, it becomes possible to achieve accurate overlay error measurement. It is possible to obtain the distance between neighboring patterns by reference to the design data; so, if a pattern having its inter-pattern distance less than or equal to the above-stated distance is found in the evaluation object region in the same layer, it may be arranged to correct a pattern shift component in accordance with the condition stored in the database. Note here that the input of distance information is not always necessary, and correction may be applied to all of the patterns in the evaluation object region.

FIG. 11 is a diagram showing one example of correction data (table) which is stored in the correction condition database 1008. This table contains the type of a pattern for use as the measuring object (Pattern Type) along with a correction quantity (Shift amount) and correction direction (Direction) per each combination of adjacent patterns. As the optical proximity effect varies with the adjacent pattern's size and distance, the correction amount and correction direction may be stored per combination thereof.

FIG. 12 is a diagram showing the positional relationship of a pattern A 1202 (upper layer pattern), pattern 1201 (lower layer pattern) and neighboring pattern b 1205. In this example, the pattern A 1202 and the pattern b 1205 are patterns in the same layer; the pattern 1201 is a lower layer pattern of these patterns. In addition, line segments 1203, 1204 and 1206 are layout data of the pattern 1201, pattern A 1202 and neighboring pattern b 1205, respectively. In the table shown in FIG. 11, there are stored the OPE-caused pattern shift amount and its direction in the case of the pattern A 1202 and its neighboring pattern b 1205 being in vicinity to each other. In the event of overlay measurement, the overlay measurement is performed after having shifted the pattern A 1202 using the correction data stored in this table, thereby making it possible to perform the overlay measurement that excludes the OPE-caused pattern shift component.

Figure 14:
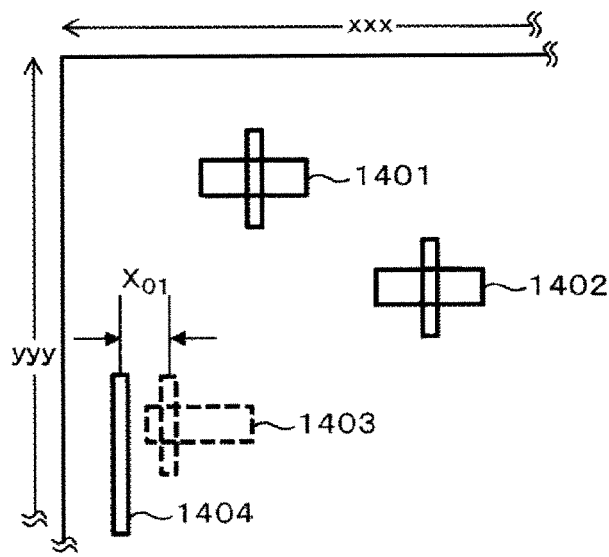
FIG. 14 A diagram shows an example of a measuring object pattern based on the overlay error measurement condition thus set up.

There is another way of thinking which follows: a pattern which is shifted by the optical proximity effect is excluded from the measuring object in light of the judgment that such pattern is inappropriate for the overlay measurement. FIG. 14 is a diagram showing one example thereof. In this example, transistors are selected as the pattern type. Transistors 1401, 1402 have no OPE-apprehensive patterns in its neighborhood. In the vicinity of a transistor 1403, a neighboring pattern 1404 is located. Among these three transistors, the transistor 1403 is the OPE pattern shift-apprehensive pattern. Consequently, a recipe may be prepared after having excluded the transistor 1403 from overlay error measuring objects in the case of $X_0 \geq X_{01}$, where $X_0$ is the input value to the window 1301 and $X_{01}$ is the distance between an upper layer pattern of the transistor 1403 on the layout data and its neighboring pattern 1404, by way of example.

(3) Image Acquisition by Execution of the Recipe

The recipe thus generated in the above-stated way is used to perform automated measurement, thereby acquiring an image that contains a pattern for use as the overlay error measuring object. The image acquired is subjected to overlay error measurement to be described later.

(4) Execution of OPE Correction

Next, in the pattern position correcting unit 1009, the position of the upper layer pattern is shifted in such a way as to correct the OPE-caused shift component. More precisely, as exemplarily shown in FIG. 12, the position of pattern A 1202 is selectively shifted based on the database-saved correction amount $(x_1, y_1)$ and correction direction $(\theta_1)$. By performing correction in this way, it is possible to perform proper evaluation even for a pattern with difficulty in performing the overlay evaluation due to a mixture of overlay error and OPE-caused pattern shift. It is also possible to obtain such overlay error only via arithmetic operation without having to shift it actually. Note that the SEM image is a line drawing with contour processing applied thereto. As for the contour data, contour lines belonging to the upper layer are selectively moved while letting contour lines belonging to the lower layer remain stationary.

(5) Overlay Error Measurement

Figure 15:
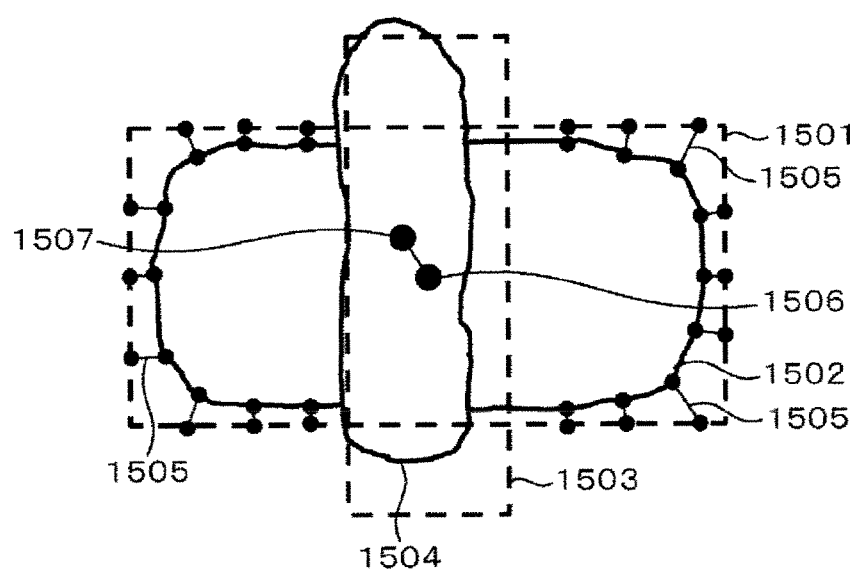
FIG. 15 A diagram shows an example which performs overlay error measurement based on dimension measurement between centroid points of patterns of different layers.

An overlay measuring unit 1010 executes overlay error measurement by using the pattern data with the OPE-caused pattern shift having been corrected at the step 4. In this case, as illustratively shown in FIG. 15, position alignment (matching) is performed between an edge 1501 of the layout data of the lower layer pattern and a contour line 1502 of the lower layer pattern; then, dimension measurement is executed between a centroid position 1506 of the edge 1503 of the layout data of the upper layer pattern with the alignment applied thereto and a centroid position 1507 of a contour line 1504 of the upper layer pattern. The alignment between lower layer patterns is executable, for example, by searching a position at which an addition average value of a distance 1505 between corresponding points of the layout data and contour line becomes minimal. Although in the block diagram shown exemplarily in FIG. 10 the pattern's position correction is performed by the pattern position correcting unit 1009 after having performed the position alignment (matching) of the layout data and contour line by the matching unit 1007, this processing order is arbitrarily determinable.

Additionally, although the reason why the part between centroids is measured is that stable measurement is enabled without depending on any possible pattern deformation or the like, the overlay error measurement may alternatively be done by measuring a distance between the layout data and the contour line's edge.

Note here that in the case of performing measurement using real patterns, it can sometimes happen that a lower layer is covered with an upper layer and, for this reason, is not represented on SEM image; in that case, the overlay measurement may be done using a pattern which has within a chip or a shot a plurality of target patterns that are specially provided for the overlay measurement (In chip overlay). In this case, it is considered that an exclusive contact hole with visibility of its lower layer is used as the dedicated target. More specifically, in the case of performing overlay measurement, it can happen that a variation (product defect such as deformation or the like) of the measurement-used real pattern per se is contained due to processing treatment (e.g., lithography process, etching process, CMP process, etc.) in semiconductor fabrication processes. Thus, in order to realize stable overlay measurement, it is desirable to perform the overlay measurement by using a specific pattern having an array of two or more optimal overlay measurement-dedicated patterns disposed within a chip or shot on a per-process basis.

Owing to recent advances in pattern microfabrication technologies, the influence of the lens aberration of a scanner used for exposure is becoming more severe when compared to the prior art; simultaneously, the influence of lens's heat accumulation due to continuous usage of the scanner is also becoming more appreciable. Thus, it is considered that different pattern shifts take place at different portions in an exposure region. Consequently, it is very effective to provide a plurality of dedicated patterns within a chip to thereby obtain a plurality of deviations.

The OPE-based pattern shift occurs at a different distance in different direction in deference to an on-sample pattern layout situation; so, in this embodiment, it is recommendable to perform deviance correction at each portion for performing accurate overlay error measurement. Additionally, in order to stably measure overlay errors, it is also recommended to obtain a statistic score (e.g., average value) of overlay errors at respective portions.

[Embodiment 2]

In this embodiment, an example will be explained which detects for estimation of position deviation due to the optical proximity effect a symmetrical pattern with respect to each of X- and Y-axes, calculates a position deviation amount from a distance between symmetrical patterns, and uses this quantity to perform position correction of an overlay measuring object pattern.

Figure 2:
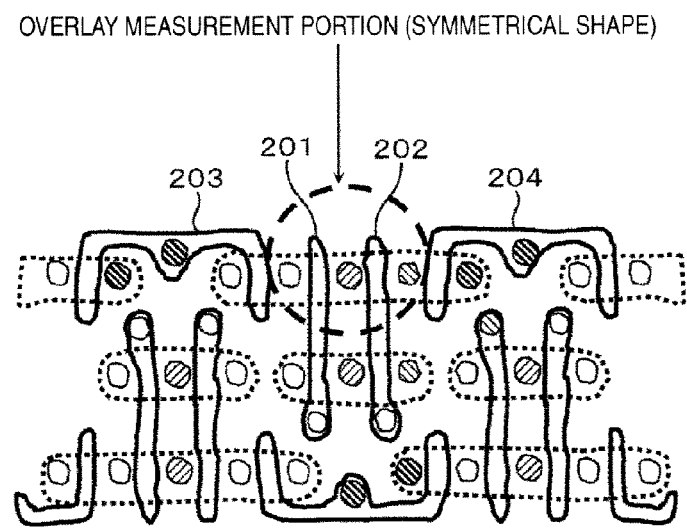
FIG. 2 A diagram shows a positional relationship of a semiconductor circuit and an overlay error measuring portion.

FIG. 2 is a diagram showing a pattern structure with six transistors disposed therein. In SRAM or like devices, the pattern structure that is illustratively shown in FIG. 2 is arrayed continuously. An upper layer (layer 2) constituting gates is arranged so that two line-like patterns 201, 202 are placed adjacent to each other as depicted herein; further, their outside patterns 203, 204 are disposed symmetrically about the center of patterns 201, 202. It is considered that the OPE of one of these symmetrical patterns such as the patterns 201, 202 with respect to the other pattern is almost the same as the OPE of the other pattern against one pattern; thus, it is very likely that the OPE-caused shift amount (absolute value) is substantially the same. Regarding the outside patterns 203, 204 also, these are disposed symmetrically about the center position of patterns 201, 202; so, the shift amount of pattern 201, 202 is considered to shift by the same quantity in opposite directions when letting the center of patterns 201, 202 be a reference.

As apparent from the foregoing, since it is considered that the OPE-caused shift of symmetrical patterns takes place in an approximately bilateral symmetrical manner, it is likely that those positions which have been symmetrically shifted so as to ensure that the distance between two patterns 201, 202 becomes identical to the design data are the positions of patterns 201, 202 in the state that the OPE-caused pattern shift is absent.

In this embodiment, an example will be explained which employs as the overlay measurement object a symmetrical pattern which is easy in recognition of OPE-caused pattern shift and which performs high-accuracy overlay error measurement after having corrected the pattern shift. In this embodiment, there will be explained an example which executes the overlay error measurement in a procedure which follows.

Step 1: Determination of overlay object pattern
Step 2: Searching symmetrical pattern
Step 3: Automatic generation of image pickup recipe
Step 4: Image acquisition for inspection and OPE correction
Step 5: OPE correction calculation processing
Step 6: Overlay measurement With this embodiment, the following technical advantages are expectable.

First of all, it is possible to realize a technique (apparatus) for directly measuring and managing the overlay of real device patterns and also possible to perform superposition evaluation which takes into consideration in-shot size irregularity occurring due to the heat aberration of the lens of an exposure device and stresses of gate portions, thereby making it expectable to achieve high yields in critical layer treatment processes.

Furthermore, it is possible to correct pattern position deviation caused by the optical proximity effect of a real device. As a result, it is possible to perform facture evaluation between layers with a lamination of contour lines of patterns acquired in a plurality of processes.

Additionally, with this embodiment, it is possible to obtain the inherently correct pattern positions for purposes of OPC calibration and validation (interpattern position correction). Therefore, by reflecting this information on OPC modeling, it becomes possible to achieve high-accuracy OPC.

Figure 6:
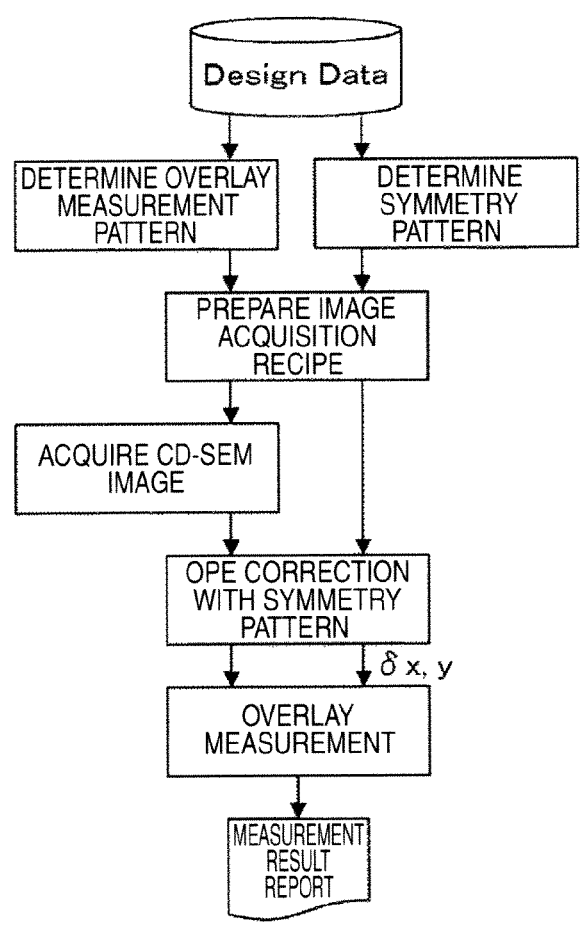
FIG. 6 A diagram shows a process of performing overlay error measurement after having selected a symmetry pattern as the evaluation object of overlay error measurement.

FIG. 6 is a diagram showing a process of performing overlay error measurement after having properly corrected the position of a symmetrical pattern (i.e., pattern having two or more adjacent patterns of the same shape) on the design data. Symmetrical pattern condition selection is performed, for example, by the input device 1004.

Step 1: Determination of Overlay Measurement Pattern

Based on the semiconductor design data (layout data), the coordinates of a superposition part of two layers and a pattern shape thereof are calculated. Then, with the use of such result, recipe information for image pickup is generated automatically.

Step 2: Symmetrical Pattern Determination

Based on the semiconductor design data (layout data), the coordinates of a symmetry pattern corresponding to the above-stated overlay measurement pattern and its pattern shape are calculated. Using such result, recipe information for image pickup is also generated automatically. The symmetrical pattern selection may be done, for example, based on a judgment as to whether patterns of the same shape are laid out within a range narrower than a predetermined distance or, alternatively, may be arranged to perform symmetrical pattern extraction by using the design data of a layout which is the basis of upper layer fabrication. The pattern selecting unit 1005 selects a pattern(s) satisfying this condition based on the symmetrical pattern condition inputted by the input device 1004.

Step 3: OPE Correction with Symmetry Pattern

Figure 7:
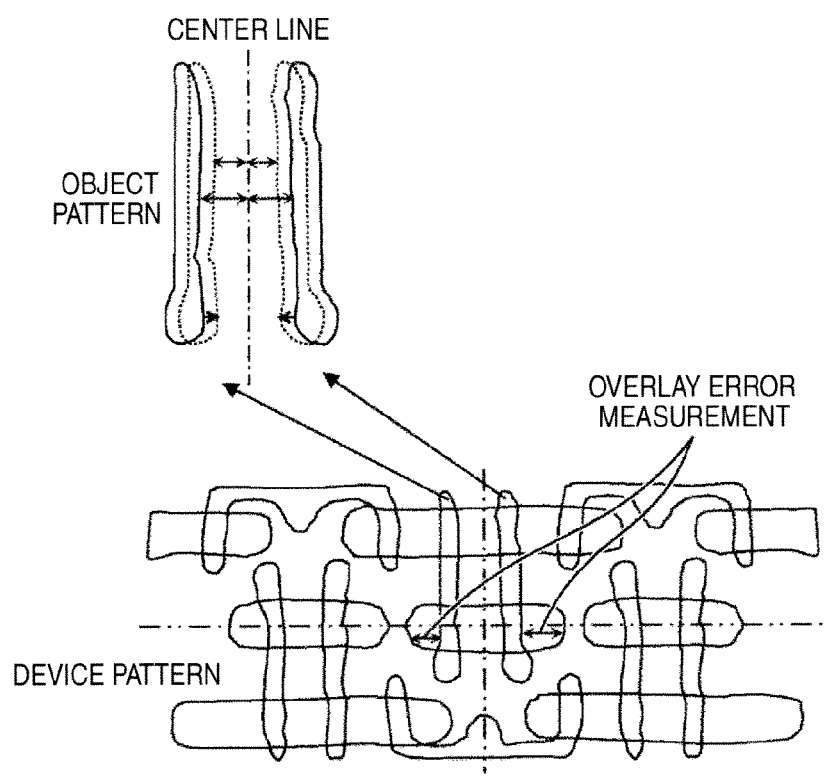
FIG. 7 A diagram shows a relationship of symmetry pattern and overlay error measurement position.

A contour shape is generated from the SEM image acquired by CD-SEM; then, correction of the position due to the influence of optical proximity effect of pattern shape is performed. FIG. 7 shows an example in which a symmetry pattern is shifted by the same degree due to the influence of optical proximity effect. As exemplarily shown in FIG. 7, the symmetry pattern is shiftable by the same degree in the right and left directions. Accordingly, in order to exclude the OPE influence, a distance (e.g., distance between centroid points) $\Delta xd$ between two patterns constituting the symmetry pattern is extracted from the design data (layout data) or simulation shape data and, simultaneously, a distance $\Delta xc$ between two patterns constituting the symmetry pattern is obtained from the contour data; then, $(\Delta xc - \Delta xd)/2$ is calculated. While letting this calculation result be a shift amount of one pattern, the pattern position correcting unit 1009 shifts the position of symmetrical pattern within the contour data.

Step 4: Overlay Measurement

Superposition is performed of the contour shape data of two layers which have been applied position correction in the above-stated step; then, overlay measurement is carried out.

As previously stated, the overlay error measurement may be arranged to obtain the distance between centroid points of patterns or, alternatively, may be arranged to measure the distance between edges. The overlay measuring unit 1010 executes overlay error measurement based on the distance between edges or centroid points with respect to the size of a field of view. In this regard, however, it is desirable to obtain a deviation between centroids in order to obtain high-accuracy deviance irrespective of any possible pattern deformation. The overlay measuring unit 1010 executes overlay error measurement from centroid or edge positions of two patterns. More specifically, in the case of performing measurement between centroid positions, a distance between the centroid of a measuring object pattern in the layout data or simulation data and the centroid of a measuring object pattern in the contour data acquired based on SEM image is obtained to thereby measure an overlay error.

Figure 8:
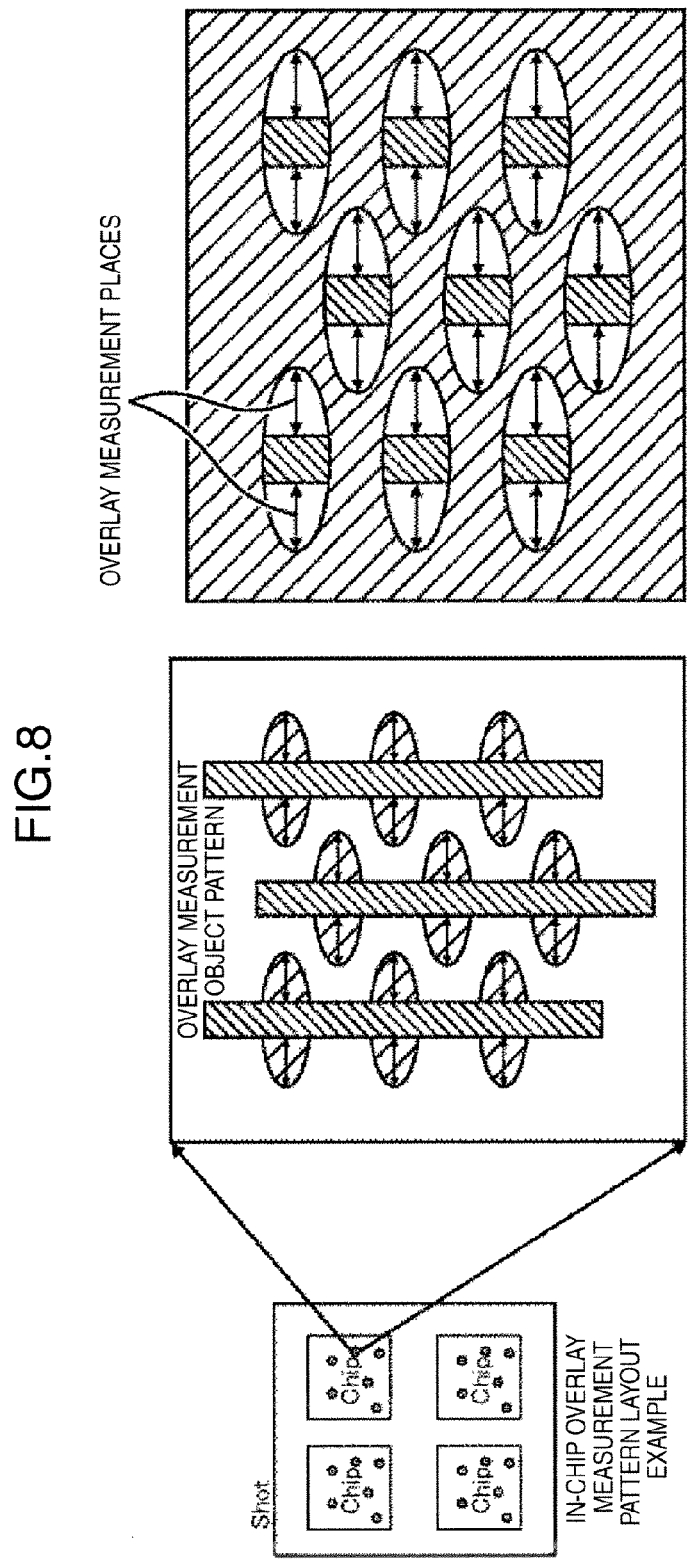
FIG. 8 A diagram shows one example of a dedicated pattern for use in overlay error measurement.

FIG. 8 shows an exemplary measurement method using dedicated patterns for exclusive use in the overlay measurement. It is the one that measures distances and widths of patterns between two upper and lower layers, wherein these patterns are measuring object patterns corresponding to this process (e.g., combinations of contact holes and wiring patterns) which have been pre-formed in empty regions of a mask of product devices. In the practical manufacturing process, there are cases where the up-down relationship of wiring lines and contact holes is covered with a dielectric film or the like, resulting in the loss of adequate visibility of the edges of two patterns serving as measuring objects in some cases. To avoid this, a structure is employed which has dedicated patterns that secure the visibility of wiring patterns at hole bottoms for example, thereby enabling detection of the pattern edges of two layers.

Regarding a rough standard of the size of this pattern, a pattern size which is represented by the minimum rule value with respect to design rules of device layers of the process is used therefor. With this approach, the overlay pattern is also fabricated under the condition that the influence is equivalent to various process influences at the time of actually manufacturing semiconductor devices. Thus, it becomes possible to achieve the intended overlay measurement with process conditions being taken into account.

Note here that this group of dedicated patterns is disposed in a plurality (e.g., several tens to a hundred) of empty spaces and dummy pattern layout areas in each chip, thereby enabling detection of the vector of in-chip pattern deviation per shot inside. This makes it possible to allow this information to be fed back to the function of exposure device control/management.

FIG. 1 shows a dedicated target pattern used for measurement of the overlay of a lower-layer pattern and a wiring line or gate pattern of an upper layer. FIG. 2 shows a dedicated pattern for overlay measurement, which includes wiring lines of the lower layer and contact holes defined in the upper layer.

According to the embodiment stated above, it is possible to use fine detection patterns when compared to optical detection devices, thus making it possible to reduce the tolerance of misalignment. It is also possible to realize, in the device level, alignment deviance management with the use of detection patterns which are the same in size as real device patterns. In addition, it becomes possible to achieve overlay error measurement free from the influence of lens aberration occurrable in optical devices. Furthermore, it becomes possible to manage the distribution in wafer surface because of an ability to measure a plurality of portions in the so-called "in-chip" manner.

Figure 3:
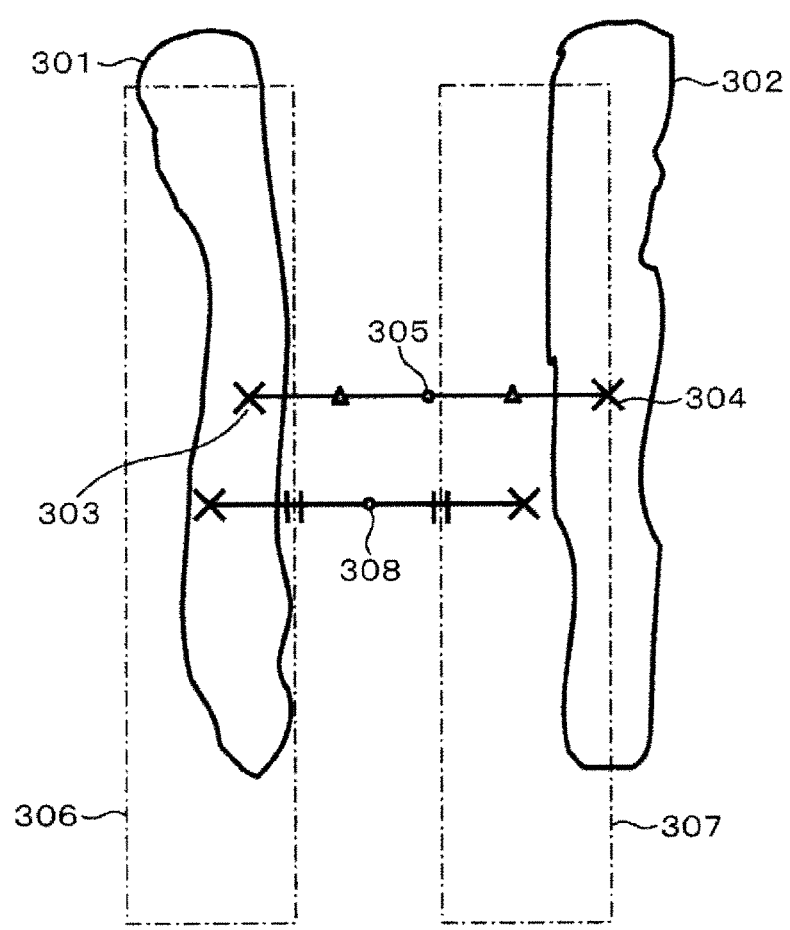
FIG. 3 A diagram shows one example of overlay error measurement using a symmetry pattern.

FIG. 3 is a diagram showing another example which performs overlay error measurement using a symmetry pattern. The OPE of one pattern included in the symmetry pattern against the other pattern therein and the OPE of the other pattern to the one pattern are considered to be almost the same; so, it is very likely that the OPE-caused shift amount (absolute value) is substantially the same. In other words, a center 305 between centroids 303, 304 of contour data 301, 302 with a mixture of overlay error and OPE-caused pattern shift is expected to reside at the same position as the center position between patterns with overlay errors only and without any OPE-caused pattern shift. Accordingly in this embodiment, the distance between the center 305 and the center 308 of reference patterns 306, 307 (graphics data of the layout data or simulation data) is determined to be the overlay error. More specifically, a difference $(\Delta x, \Delta y)$ between the coordinates $(x_{305}, y_{305})$ of the center 305 and the coordinates $(x_{308}, y_{308})$ of center 308 is qualified as the quantity of an overlay error while letting $A\tan(\Delta y/\Delta x)$ be the direction of such overlay error.

With this arithmetic computation, it becomes possible to achieve the overlay error measurement that excludes the OPE influence regardless of the actual significance of OPE.

[Embodiment 3]

To perform overlay error measurement with increased accuracy, it is required to acquire images at high magnification ratios (with narrow field-of-view size). On the other hand, when an attempt is made to perform such image acquisition with large magnification, it can sometimes happen that upper and lower layer patterns fail to be received within a single view field. Consequently, an example will be explained which performs overlay measurement by using panorama techniques for joining or "splicing" together those images acquired at high magnification ratios to thereby create a high-resolution image in a wide-ranging area.

Figure 4:
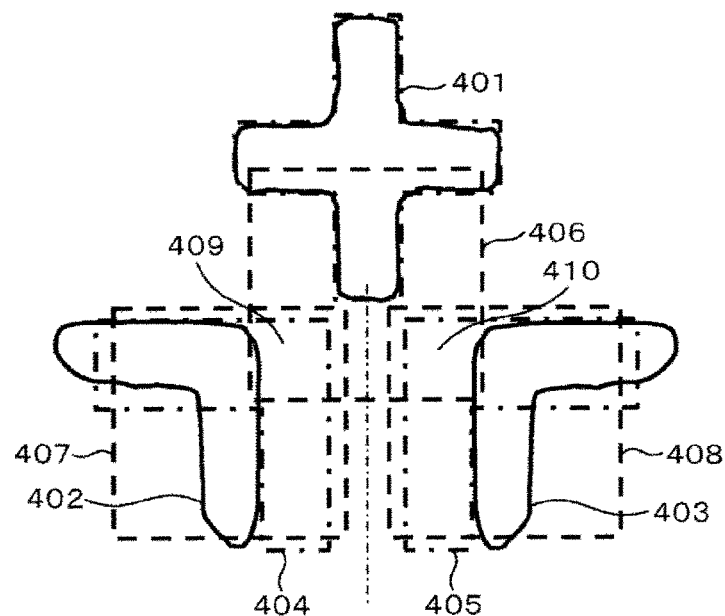
FIG. 4 A diagram shows a positional relationship of a symmetry pattern and a plurality of field-of-view positions in the event of forming a panorama image.

In the case of forming a panorama image, if there is an OPE-caused pattern shift such as explained in Embodiment 2, a pattern fails to reside at its inherently expected position; thus, there is a risk that the image splicing is failed. FIG. 4 is a diagram showing one example of a circuit pattern with a lower layer pattern 401 and upper layer patterns 402, 403 being disposed therein. View fields 407, 408 are set in conformity to the positions of layout data 404, 405; superimposed regions 409, 410 with a view field 406 containing the pattern 401 are set up. A superimposed portion between view fields is required to contain edges in at least two directions in order to perform the splicing accurately. The reason of this is as follows: if all edges are in only one direction then it is no longer possible to specify two-dimensional positions.

Explained below is an example which sets view fields at appropriate positions by reference to the database as has been explained in Embodiment 1 in order to enable accurate splicing.

Figure 5:
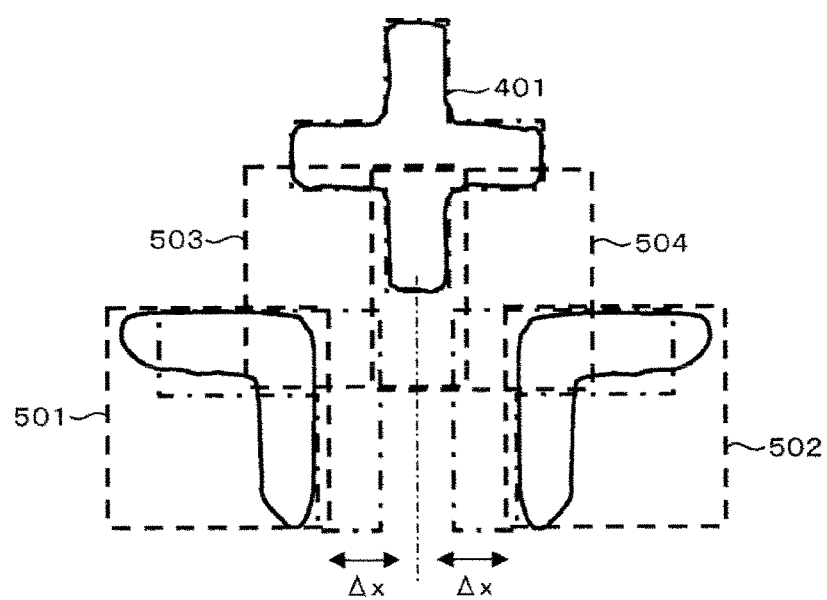
FIG. 5 A diagram shows an example which corrects field-of-view positions in a way tracking an OPE-caused symmetry pattern shift.

FIG. 5 is a diagram showing an example which sets view fields by taking into consideration pattern shift components. As shown herein, a view field 501, 502 is the one that is obtained by shifting view field 407, 408 by a degree corresponding to the pattern shift while referring to the database shown exemplarily in FIG. 11. In FIG. 5, there is shown an example which has shifted each pattern by Δx with respect to its initial view-field setup position (view field 407, 408).

Figure 16:
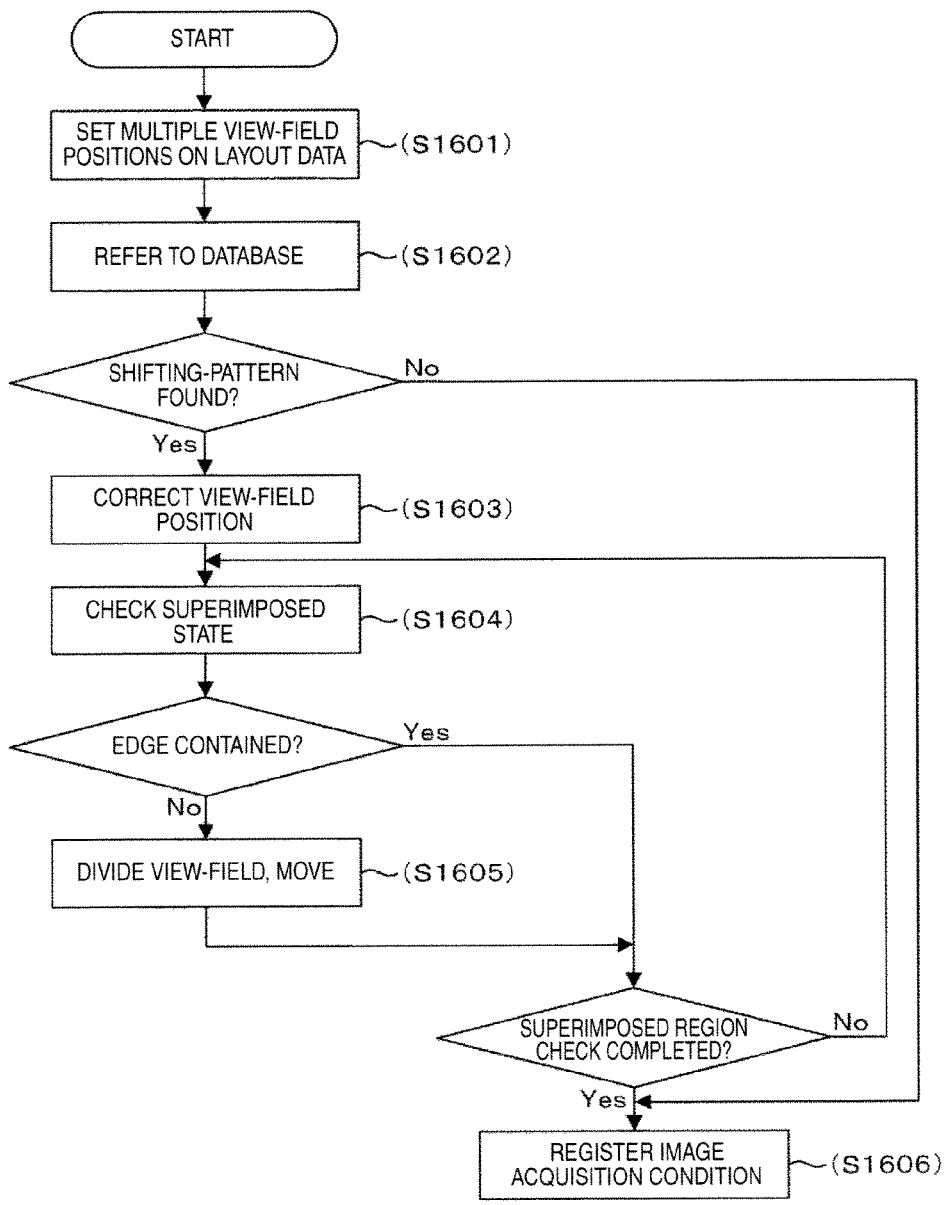
FIG. 16 A flowchart shows a field-of-view position setting process for panorama image formation.

FIG. 16 is a flowchart showing a process of correcting the initial setup positions of view fields by reference to the database in the event of creating a panorama image.

Firstly, as exemplarily shown in FIG. 4, a plurality of view fields for creation of a panorama image on the layout data are set up (at step 1601). In this case, care should be taken to provide a superimposed region between the plurality of view fields and, simultaneously, cause the superimposed region to contain at least two-directional line segments. Next, by referring to the database exemplarily shown in FIG. 11 (step 1602), judgment is made to determine whether an OPE-caused pattern shift-generating one is present in the panorama image-forming region. If such pattern shift-generating pattern is found then move the view-field position based on the shift amount and its direction stored in the database.

Next, the state of superposition is checked between the field of view (view field 406) in which one part of the view field has been superimposed prior to position correction and the moved view field (step 1604). In a case where it is possible to judge that an edge needed for position alignment is not contained (when two-direction edges are not contained, when the view field is smaller than a predetermined size (when the superimposed regions is too small to retain the superposition accuracy), etc.), the view field 406 is divided to set up view fields 503, 504; simultaneously, the position of view field 406 is shifted by Δx in such a way as to follow up the view fields 501, 502 (at step 1605). In this case, even when the shift amount <Δx, if it is possible to judge that an edge needed for position alignment is contained in the superimposed region, the view field 503, 504 may be moved by a degree corresponding to such shift amount.

Furthermore, the state of another superimposed region resulting from the view-field movement is checked; when it is judgeable that an edge is properly contained in the superimposed region, registration is done as an image pickup recipe of SEM with the setup or corrected view-field position being as one of the image acquisition conditions (step 1606). This imaging recipe is stored in a storage medium, such as a memory which is built in the control device 914 or the input device 1004 for example, and is read out as an operation program at the time of SEM activation.

With the above-stated arrangement, it becomes possible to set view fields at appropriate positions regardless of the presence of OPE. Additionally, in the case of performing overlay error measurement, it becomes possible to perform high-accuracy overlay error measurement using a plurality of patterns extending to cover a wide range.

[Embodiment 4]

Next, an explanation will be given of an example which sets a panorama image-forming condition by using simulation data. The simulation data is the one that is obtained as a result of applying to the layout data stored in design data storage medium 1002 pattern shape prediction with additive use of the pattern-forming condition and others. The operation is performed by the simulator 1003.

An important point in the process for setting the panorama image-forming condition lies in causing the acquired image (field of view) to have an appropriate overlapping portion (superimposed region) as stated supra. To optimally dispose this FOV position with the design data being as a reference, it is necessary to take into consideration the OPE-caused pattern deformation and shift.

In this embodiment, an explanation will be given of an example which obtains the degree of divergence of a simulation shape and a layout shape based on design data and then sets a field of view (FOV) at a suitable position. More specifically, an example will be explained which evaluates the facture of each portion of a pattern based on a result of edge placement error (EPE) length-measurement between corresponding points (i.e., those points capable of being assumed to be the same portion of the pattern) of the layout data and simulation data, and sets field-of-view positions in accordance with this facture.

Figure 17:
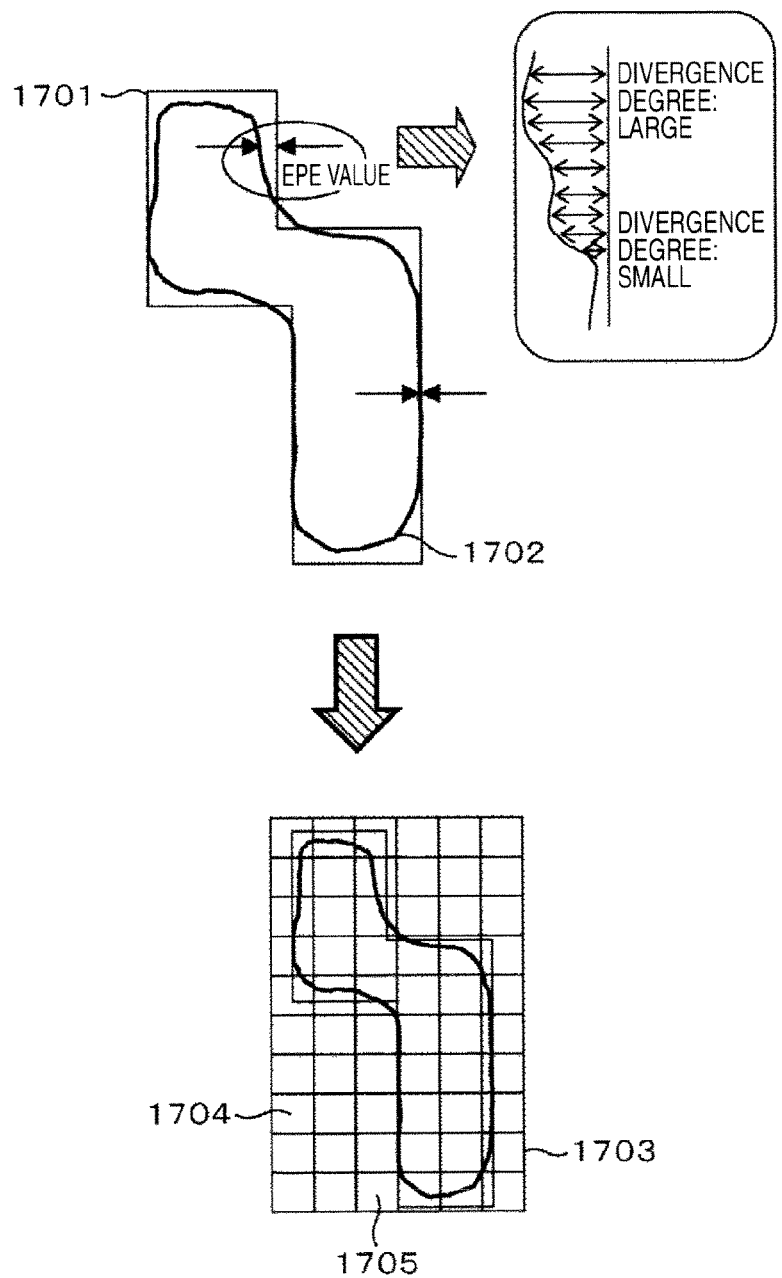
FIG. 17 A diagram shows an example which prepares an evaluation map (divergence map) of layout data and simulation data based on an EPE length-measurement result.

FIG. 17 is a diagram showing an example which calculates an evaluation value (in this example, the divergence degree between both shapes) of each portion of the pattern based on an EPE length-measurement result (EPE value) between a layout shape 1701 and simulation shape 1702 and prepares an evaluation map 1703 based on the evaluation value computation. The evaluation map is for dividing the pattern into a matrix of rows and columns and for storing evaluation values as to respective portions thereof. The evaluation value of each portion is handleable as an EPE length-measurement result belonging to this portion or an average value of EPE length-measurement results belonging to the portion.

Figure 18:
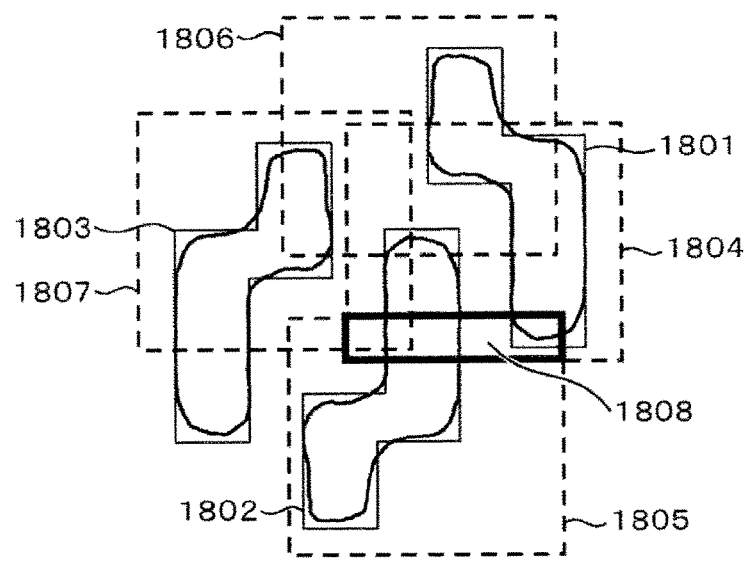
FIG. 18 A diagram shows a positional relationship of a plurality of field-of-view positions which are set up for panorama image formation.
Figure 20:
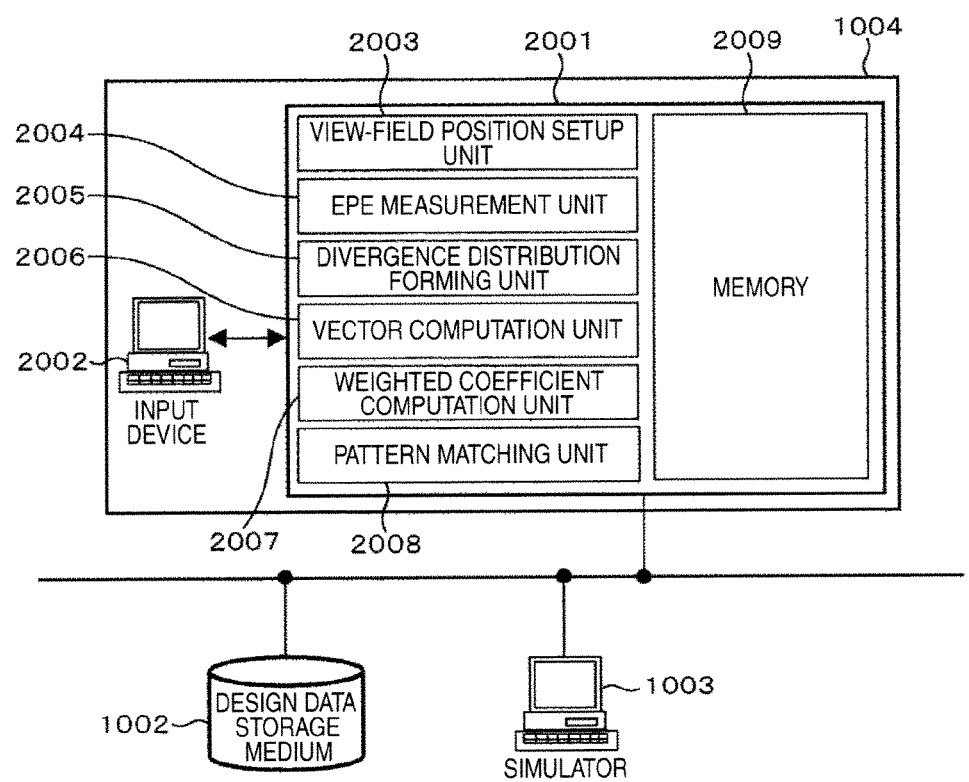
FIG. 20 A diagram shows one example of a panorama image formation condition setup device.

FIG. 20 is a diagram showing an overview of an image pickup recipe creation system functioning as SEM image pickup recipe preparation device, which includes an input device 1004, design data storage medium 1002 and simulator 1003. The input device 1004 has an arithmetic processing device 2001 and an input unit 2002. A view-field position setup unit 2003 included in the arithmetic device 2001 sets a view field or fields based on the condition inputted from the input unit 2002. Examples of the condition for forming a panorama image of three patterns 1801 to 1803 shown exemplarily in FIG. 18 are the size (magnification ratio) of a view field, the size of a superimposed region and other optics conditions of SEM, which are inputted from the input unit 2002. Also note that while in the example of FIG. 18 several view fields 1804, 1805, 1806 and 1807 are sequentially set from the right side of the drawing, this image acquisition order is also inputtable.

As exemplarily shown in FIG. 17, an EPE measurement unit 2004 measures the dimension of a part between the layout shape 1701 and simulation shape 1702 with respect to a plurality of portions of the pattern. A divergence distribution forming unit 2005 calculates based on an EPE length-measurement result thus obtained the degree of divergence of the layout data and simulation data with a predetermined region being as a unit. More specifically, it obtains an index value indicating the divergence degree of the both, such as an EPE value per each portion, average value or weighted average value or the like, and then registers it to a memory 2009 with a portion 1704, 1705 of evaluation map 1703 being as a unit, by way of example.

A vector computation unit 2006 performs vector calculation of edges contained in a superimposed region 1808 between view fields, for example, thereby calculating a distribution of horizontal components (x components) and vertical components (y components). For example, it executes arithmetic processing to determine how many x components are contained in the edges included in the superimposed region 1808 and how many x components are contained therein. A weighted coefficient computation unit 2007 sets a weighted coefficient based on the index value obtained at the divergence distribution forming unit 2005.

Figure 19:
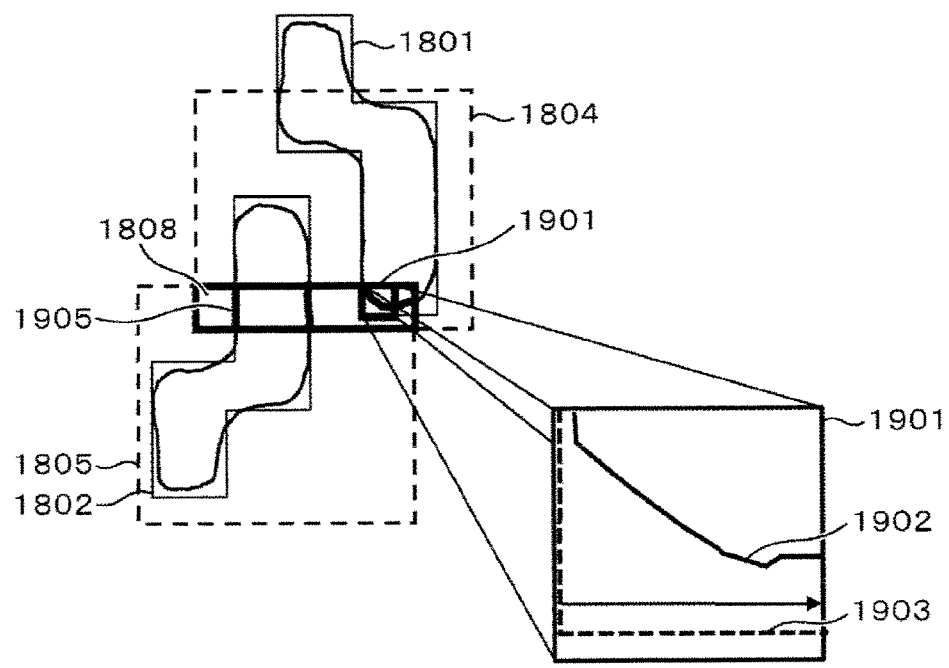
FIG. 19 A diagram shows for explanation of an example which evaluates a superimposed region between a plurality of view fields for panorama image creation.

FIG. 19 is a diagram showing an example which performs evaluation of the superimposed region 1808 of view fields 1804, 1805 shown exemplarily in FIG. 18. For example, based on the index value at a portion 1901, the divergence distribution forming unit 2005 sets the weighted coefficient. More specifically, a portion which is large in the divergence of simulation data and layout data is considered to be a portion at which a real pattern shape is unstable and thus a predefined edge shape is not obtainable. So, vector computation is performed at each portion (e.g., portion 1901) to calculate an index value relating to existential quantities of x- and y-direction components; concurrently, a coefficient of the index value is set in accordance with the degree of divergence between the layout data 1904 and simulation data 1902. The greater the divergence degree, the smaller the weighted coefficient.

When an accumulated value of "index value x weighted coefficient" in the x- and y-directions of a plurality of portions contained in the superimposed region 1808 satisfies a predetermined condition (i.e., the state judgeable to have enabled establishment of line segments enough for super-position in both of x- and y-directions), the view field setup unit 2003 registers the position of such view field to memory 2009 as the image acquisition condition.

A pattern matching unit 2008 executes pattern matching between the layout data and simulation data, between the simulation data and SEM image-based edge data (e.g., contour data extracted from SEM image) or between the layout data and SEM image-based edge data.

Figure 21:
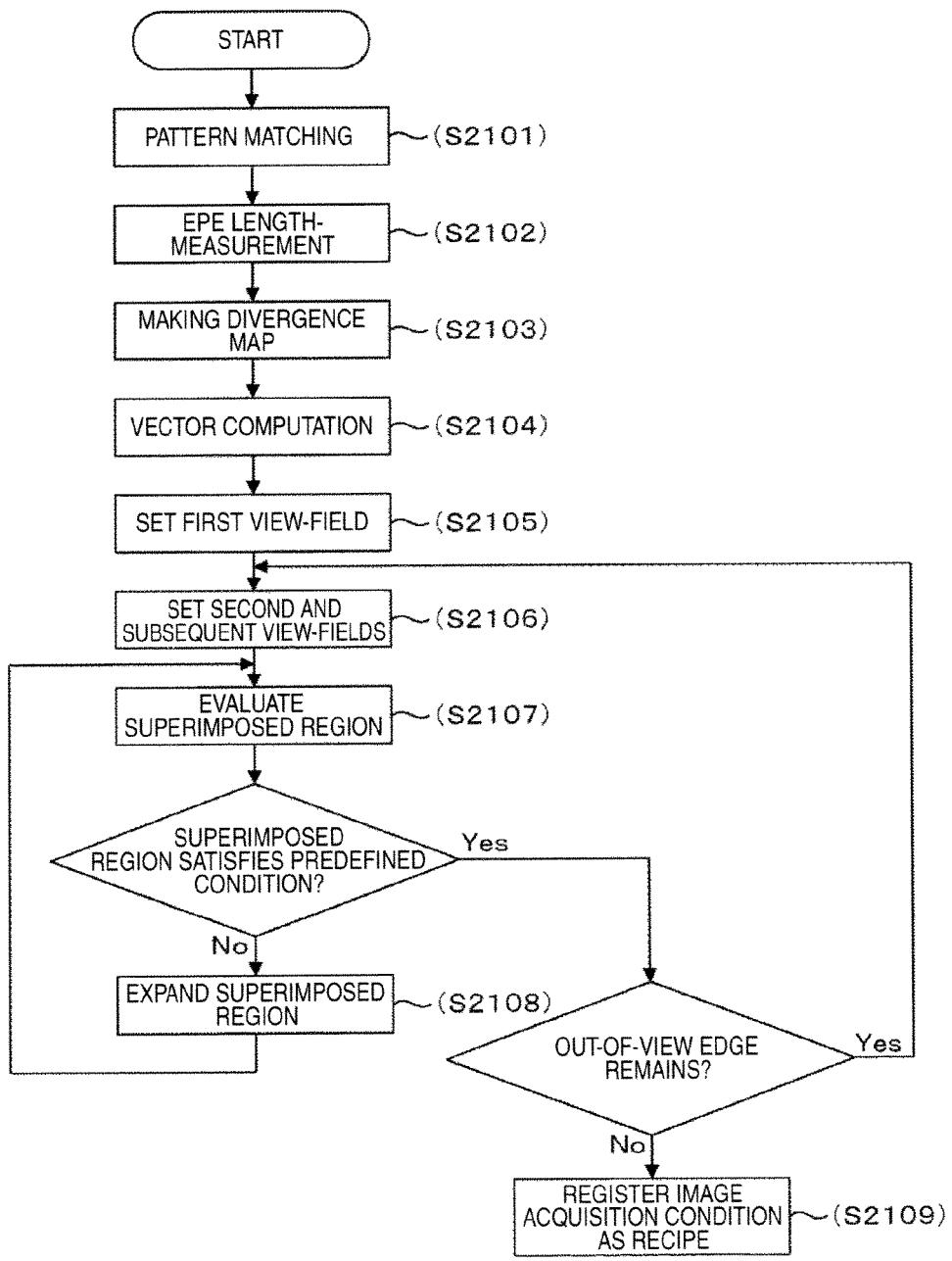
FIG. 21 A flowchart shows a panorama image formation condition setup process.
Figure 22:
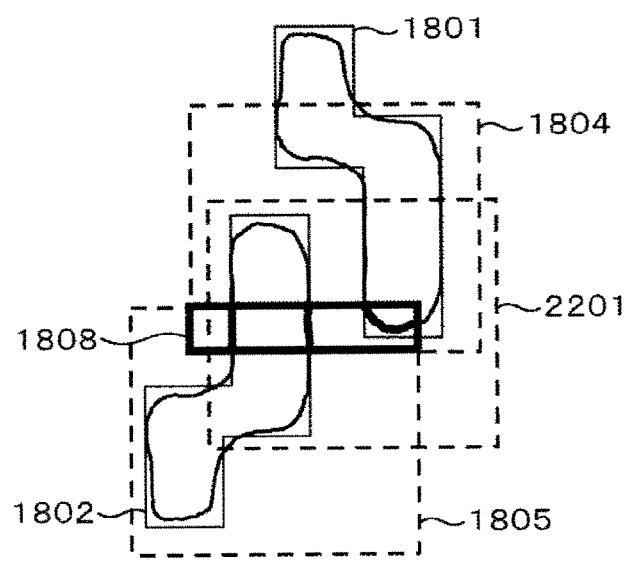
FIG. 22 A diagram shows an example which sets up a new field of view between a plurality of view fields for panorama image formation.

FIG. 21 is a flowchart showing a process of selecting view fields for creation of a panorama image.

Firstly, the layout data stored in the design data storage medium 1002 and the simulation data prepared by the simulator 1003 are read out to execute pattern matching between them (at step 2101). Next, it executes dimension measurement (EPE length-measurement) between corresponding points of the layout data and simulation data (step 2102). Based on this EPE length-measurement result, it applies mapping to the divergence situation per pattern portion (step 2103). Next, it performs vector calculation of edges with respect to simulation shape, thereby computing a distribution of x-direction line segments and y-direction line segments (step 2104). Next, based on designated view-field size and panorama image creation object region information, it sets a first view field (e.g., field 1804 of FIG. 18) (step 2105). In the case of the example of FIG. 18, the initial condition is set in such a manner that view fields are sequentially arrayed from the right side of the drawing while causing the right-side end of view field 1804 to reside at a predetermined distance from an edge on right side of pattern 1801. Setting is also done to ensure that a superimposed region of the pattern 1801 and the view field 1804 becomes the largest under the condition stated above.

Next, a second view field is set (step 2106). The second view field (field 1805) is so set as to make sure that the pattern 1802 is maximally received within the view field while simultaneously providing a superimposed region of a predetermined size along with the first view field. At this time, regarding the superimposed region 1808, judgment is made to determine whether predetermined line segment information is included therein as stated previously (step 2107). In case it is possible to judge that none is included, the size of the superimposed region 1808 is enlarged (step 2108).

In this case, when it is possible to judge that a line segment in x-direction is not included sufficiently in the superimposed region 1808 for example, the view field 1805 is shifted to the right side, thereby causing a greater part of x-direction line segment (lower end portion of pattern 1801) of the superimposed region 1808 to be included in the superimposed region 1808. Alternatively, the view field 1805 may be shifted upwardly to ensure that an upper end portion of the pattern 1802 is included in the superimposed region 1808. In the case of the example of FIG. 18, in order to cause more x-direction line segment to be included in the superimposed region, x-direction line segments in the vicinity of the superimposed region are searched for selecting a specific view-field position which guarantees that the size of superimposed region becomes the smallest. The larger the superimposed region, the greater the number of acquired images. Thus, based on the above-stated judgment criteria, the view field 1805 is selected to make sure that the superimposed regions becomes smaller while containing a predefined line segment(s).

In the case of shifting the view field 1805, it is possible by alternately performing the shifting and the evaluation of superimposed region to select an adequate view-field position without having to excessively enlarging the size of superimposed region. Additionally, in cases where part of the pattern 1802 protrudes undesirably from the view field 1805 as a result of the movement of the view-field setup position, an attempt is made to select a new view field in order to acquire the image of such protruded part.

By repeated execution of the setting of a new field of view and superimposed region evaluation/correction operations in the way stated above, it is possible to find out the image acquisition condition capable of realizing connection between images with high accuracy while suppressing unwanted increase in number of view fields.

In the case where it was able to judge that all desired pattern edges are received within the view field(s) via the above-stated process steps, the resultant image acquisition condition is registered as a recipe to the memory 2009 or the like.

[Embodiment 5]

In the case of composing together a plurality of images in order to create a panorama image, if the number of those edges within the superimposed region is not sufficient then the accuracy of position alignment decreases in some cases. This can occur due to some reasons including the facture of transfer patterns, the influence to stage accuracy of image pickup apparatus, etc.

To complement such state, in this embodiment, an example will be explained which sets a new view field 2201 between the view fields 1804 and 1805. By newly setting the view field 2201, it becomes possible to get and hold a sufficient number of edges in the superimposed region.

In this case, the sequence of superimposing process operations is important in order to enhance the position accuracy of superposition. In the case of this example, superposition processing is executed in an order of view field 1804→view field 2201→view field 1805. This execution order is obtainable by analyzing the design data or simulation data and evaluating the reliability and easiness of connection of respective edges.

Additionally, concerning those edges contained in the superimposed region 1808, evaluation is performed in the way stated above in the previous embodiments; when it is possible to judge that a predetermined condition is not satisfied, the view field 2201 is selectively increased, thereby making it possible to perform high-accuracy composition processing with the minimum necessary number of view fields.

REFERENCE SIGNS LIST

901 Electron Source
902 Pullout Electrode
903 Electron Beam
904 Condenser Lens
905 Scan Deflector
906 Objective Lens
907 Vacuum Chamber
908 Sample Table
909 Sample
910 Electron
911 Secondary Electron
912 Conversion Electrode
913 Detector
914 Control Device

The invention claimed is:

1. An overlay error measuring device having an arithmetic processing device for performing measurement of a pattern formed on a sample based on an image obtained by a charged particle beam device, wherein
the arithmetic processing device uses a signal obtained by the charged particle beam device to measure dimensions between a plurality of patterns belonging to different layers and, during the measurement of dimensions, corrects a pattern shift component due to an optical proximity effect to thereby execute dimension measurement between the plurality of patterns, and
the arithmetic processing device selects a symmetry pattern as the dimension measuring object pattern.

2. The overlay error measuring device according to claim 1, wherein the arithmetic processing device executes dimension measurement between the plurality of patterns after having corrected a distance between two patterns constituting the symmetry pattern in such a way that it becomes the same as the symmetry pattern's layout data or simulation data.

3. The overlay error measuring device according to claim 1, wherein the arithmetic processing device measures dimensions of a midpoint between two patterns constituting the symmetry pattern of layout data or simulation data and a midpoint between two patterns constituting the symmetry pattern of contour data to be generated based on a signal obtained by the charged particle beam device.

4. The overlay error measuring device according to claim 1, wherein the arithmetic processing device executes the dimension measurement between the plurality of patterns based on a panorama image with a plurality of fields of view composed together.

5. The overlay error measuring device according to claim 4, wherein the arithmetic processing device selects a symmetry pattern as the dimension measuring object pattern.

6. The overlay error measuring device according to claim 5, wherein the arithmetic processing device causes the field of view to move in accordance with a shift of the symmetry pattern.

7. The overlay error measuring device according to claim 6, wherein the arithmetic processing device moves the field of view in such a way that a predetermined edge is contained within a superimposed region between the plurality of fields of view.

8. A computer program for allowing a computer to execute measurement of patterns formed on a sample based on an image obtained by a charged particle beam device, wherein
the computer program causes the computer to use a signal obtained by the charged particle beam device to measure dimensions between a plurality of patterns belonging to different layers and to correct, during the measurement of dimensions, a pattern shift component due to an optical proximity effect to thereby execute dimension measurement between the plurality of patterns, and
the computer program causes the computer to select a symmetry pattern as the dimension measuring object pattern.

* * * * *